United States Patent [19]

Butts

[11] Patent Number: 4,782,188

[45] Date of Patent: Nov. 1, 1988

[54] PROCESS FOR HYDROFORMYLATION OF UNSATURATED COMPOUNDS USING IRON CARBONYL CATALYSTS

[75] Inventor: Susan B. Butts, Midland, Mich.

[73] Assignee: The Dow Chemical Company, Midland, Mich.

[21] Appl. No.: 551,759

[22] Filed: Nov. 14, 1983

[51] Int. Cl.$^4$ .............................................. C07C 45/00
[52] U.S. Cl. ..................... 568/444; 568/429; 568/451; 568/813; 568/819; 568/909
[58] Field of Search ............... 568/444, 428, 451, 429, 568/813, 819, 909

[56] References Cited

U.S. PATENT DOCUMENTS

| | | |
|---|---|---|
| 1,562,480 | 11/1925 | Wietzel et al. |
| 2,527,846 | 10/1950 | Phinney et al. |
| 2,691,046 | 10/1954 | Hasek |
| 3,254,023 | 5/1966 | Miale et al. ........................ 208/120 |
| 3,965,192 | 6/1976 | Booth |
| 4,176,234 | 11/1979 | Grasselli et al. .................... 562/546 |
| 4,199,478 | 4/1980 | Mantovani et al. |

OTHER PUBLICATIONS

Kang et al., V.A.C.S. 99 (1977) 8323–8325.

Palagyi et al., Jour. of Organometallie Chem. 236 (1982) 343–347.

Reppe et al., Justus Liebigs Ann. Chem. 582 (1953) 133–161.

*Primary Examiner*—Donald B. Moyer
*Assistant Examiner*—Bruce D. Gray

[57] ABSTRACT

The invention is a process for the hydroformylation of $C_{2-4}$ alkenes, formyl-substituted $C_{2-4}$ alkenes, aryl-substituted alkenes, unsaturated norbornane ring-containing compounds, and α-unsaturated acetals which comprises contacting a $C_{2-4}$ alkene, a formyl-substituted $C_{2-4}$ alkene, aryl-substituted alkene, an unsaturated norbornane ring-containing compound or an α-unsaturated acetal in a polar organic solvent with water and carbon monoxide in the presence of a catalytic amount of a catalyst which comprises a mixture of (a) an alkali metal iron carbonyl or alkaline earth metal iron carbonyl which corresponds to the formula $M_aFe_x(CO)_y$ and (b) iron pentacarbonyl under conditions such that an alcohol or aldehyde derivative of a $C_{2-4}$ alkene, a formyl-substituted $C_{2-4}$ alkene, an aryl-substituted alkene, unsaturated norbornane ring-containing compound or an α-unsaturated acetal, is prepared wherein M is an alkali metal or alkaline earth metal; a is 1 or 2; x is an integer of 2 to 4, inclusive; and y is 8, 11 or 13.

21 Claims, No Drawings

PROCESS FOR HYDROFORMYLATION OF UNSATURATED COMPOUNDS USING IRON CARBONYL CATALYSTS

BACKGROUND OF THE INVENTION

This invention relates to a novel process for the hydroformylation of certain unsaturated compounds. More specifically, it relates to the use of certain iron carbonyl catalysts.

The hydroformylation of olefins with hydrogen and carbon monoxide is a well-known process. Most known processes require the use of rhodium or cobalt in various forms as catalysts. These processes are generally run at elevated temperatures and pressures, for example, about 125° C. to 175° C. and about 3000 to 5000 psig. Cobalt- and rhodium-based catalysts are expensive and often render processes using them uneconomical. Furthermore, many of these catalysts require stringent conditions in order to be operable.

As a result of these problems many researchers have attempted to use other catalyst systems for hydroformylation of olefins. An olefin can be converted to the next higher alcohol by reaction with water and carbon monoxide in the presence of a catalyst comprising a Bronsted or Lewis base and iron pentacarbonyl under relatively mild temperatures and pressures. W. Reppe et al., *Justus Liebigs Ann. Chem.*, 582 133 (1953). Kang et al., *J. Am. Chem. Soc.*, 99 8323 (1977), disclose that the presence of a strong base is necessary for iron pentacarbonyl to be catalytic in he Reppe synthesis. In hydroformylation reactions, carbon dioxide is a by-product which reacts with the base to deactivate the catalytic system. Such side reactions result in significant reductions in the number of times the catalyst can be regenerated. As a result, these processes requre large amounts of base for the catalyst to continue its catalytic activity.

What is needed is a catalyst system for hydroformylation of olefins which does not contain expensive metals such as cobalt or rhodium and which requires mild reaction conditions. What is further needed is a process which retains its catalytic activity for extended periods of time without the use of large amounts of base.

SUMMARY OF THE INVENTION

The invention is a process for the hydroformylation of $C_{2-4}$ alkenes, unsaturated norbornane ring-containing compounds, and α-unsaturated acetals which comprises contacting a $C_{2-4}$ alkene, a formyl-substituted $C_{2-4}$ alkene, an aryl-substituted alkene, an unsaturated norbornane ring-containing compound or an α-unsaturated acetal in a polar organic solvent with water and carbon monoxide in the presence of a catalytic amount of a catalyst which comprises a mixture of (a) an alkali metal carbonyl, alkaline metal carbonyl or a mixture thereof which corresponds to the formula $M_a[Fe_x(CO)_y]$ and (b) iron pentacarbonyl under conditions such that an alcohol or aldehyde derivative of a $C_{2-4}$ alkene, $C_{2-4}$ formyl-substituted alkene, an aryl-substituted alkene, an α-unsaturated norbornane ring-containing compound, or an α-unsaturated acetal is prepared, wherein M is an alkali metal or alkaline earth metal; a is the integer 1 or 2; x is an integer of from 2 to 4 inclusive; and y is the integer 8, 11 or 13.

In another aspect the invention is a hydroformylation catalyst which comprises (a) an iron carbonyl compound which corresponds to the formula $M_a[Fe_x(CO)_y]$ and (b) iron pentacarbonyl wherein M, x and y are as defined hereinbefore.

The novel catalyst of this invention does not require the presence of large amounts of base to retain its catalytic activity for extended periods of use. The reaction conditions require for catalytic activity are relatively mild. Furthermore, these iron-based catalysts are less expensive than the cobalt- and rhodium-containing catalysts of the prior art.

DETAILED DESCRIPTION OF THE INVENTION

The novel hydroformylation catalysts of this invention have catalytic activity for only selected olefins. These olefins are $C_{2-4}$ alkenes, a formyl-substituted $C_{2-4}$ alkene, an aryl-substituted alkene, unsaturated norbornane ring-containing compounds, and α-unsaturated acetals.

The $C_{2-4}$ alkenes, formyl-substituted $C_{2-4}$ alkenes and aryl-substituted alkenes useful in this invention include those corresponding to the formula

wherein $R^1$ is separately in each occurrence hydrogen, methyl, ethyl, a formyl group, a phenyl group, or a phenyl group substituted with an alkyl, aryl, formyl, halo, nitro, cyano, alkoxy or aryloxy group. Examples of alkenes useful in this invention include ethylene, propylene, 1-butene, 2-butene, styrene, 2-propenal and 2-butenal.

The unsaturated norbornane ring-containing compounds include any compounds which contain a norbornane ring in which the norbornane ring contains unsaturation. Included among such compounds are those which correspond to the formulas

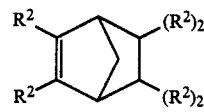

and

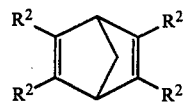

wherein $R^2$ is separately in each occurrence hydrogen, a hydroxymethyl, a formyl group or a $C_{1-20}$ hydrocarbyl group. $R^2$ is preferably hydrogen, a formyl or $C_{1-10}$ alkyl group, even more preferably hydrogen, a formyl or $C_{1-3}$ alkyl group, and most preferably hydrogen or a formyl group. Examples of compounds useful in this invention include norbornene, norbornene carboxaldehyde, norbornanediene and dicyclopentadiene.

The α-unsaturated acetals include compounds which contain an acetal functionality and unsaturation on the carbon atom α to the acetal carbon atom. Such compounds which are useful in this invention include those which correspond to the formula

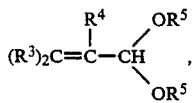

wherein R³ is separately in each occurrence hydrogen or C₁₋₂₀ alkyl; R⁴ is hydrogen or methyl; and R⁵ is separately in each occurrence a C₁₋₂₀ hydrocarbyl group, or the R⁵'s may combine to form a cyclic acetal ring.

R³ is preferably hydrogen or C₁₋₂₀ alkyl, more preferably hydrogen or C₁₋₃ alkyl, even more preferably hydrogen or methyl and most preferably hydrogen.

R⁵ is preferably C₁₋₂₀ alkyl, more preferably C₁₋₃ alkyl, and most preferably methyl or ethyl. Examples of compounds useful in this process include 3,3-dimethoxy-1-propene; 3,3-diethoxy-1-propene; and 3,3-dimethoxy-2-methyl-1-propene.

In general, the products of this invention are aldehyde-(formyl) or alcohol-(phydroxymethyl) substituted derivatives, or mixtures thereof, of the olefins described hereinbefore. Specifically, either a formyl or hydroxymethyl moiety is inserted at the point of unsaturation.

When the olefin is a C₂₋₄ alkene, the product is a C₃₋₅ alkanol, a C₃₋₅ alkanal or mixtures thereof. When the olefin is a formyl-substituted C₂₋₄ alkene, the product is a C₃₋₅ alkanediol, a C₃₋₅ alkanedial or a mixture thereof. Under the conditions wherein an alcohol moiety is added, the formyl moiety undergoes hydrogenation to prepare an alcohol moiety. When the olefin is an aryl-substituted alkene, the product is an aryl-substituted alkanal, an aryl-substituted alcohol or a mixture thereof. The C₃₋₅ alkanols, C₃₋₅ alkanediols and aryl-substituted alcohols correspond to the formula

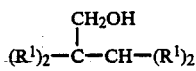

and the C₃₋₅ alkanals, C₃₋₅ alkanedials and aryl-substituted alkanals correspond to the formula

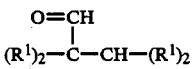

wherein R¹ is as defined hereinbefore.

Examples of alcohols prepared by this process include propanol, butanol and pentanol. Examples of alkanals prepared include propanal, butanal or pentanal.

The process conditions can be adjusted to give the desired product mix, that is, alkanols, alkanals, or a particular mixture thereof. In particular, the reaction temperature is critical to the product mix. Alkanols are the preferred products. In those embodiments wherein the alkene contains unsaturation on a terminal carbon atom, the process of this invention prepares primarily straight-chained alkanols and alkanals.

In the embodiment wherein an unsaturated norbornane ring-containing compound is the olefin, the products of the invented process are formyl-substituted norbornane ring-containing compounds, hydroxymethyl-substituted norbornane ring-containing compounds, or mixtures thereof. The hydroxymethyl-substituted norbornane ring-containing compounds include those corresponding to the formula

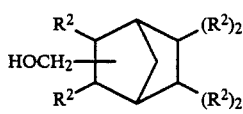

and the formyl-substituted norbornane ring-containing compound corresponds to the formula

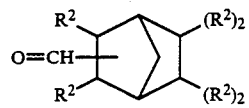

wherein R² is as defined hereinbefore. Examples of compounds prepared by this process include norbornane carboxaldehyde, norbornane methanol, norbornane dicarboxaldehyde and norbornane dimethanol. The preferred products of the process of this invention are the hydroxymethyl-substituted compounds.

In the embodiment wherein the unsaturated norbornane ring-containing compound is dicyclopentadiene, the process of this invention selectively hydroformylates the unsaturated point on the norbornane ring without hydroformylating the unsaturation of the other ring.

In the embodiment wherein the unsaturated norbornane ring-containing compound is substituted with a formyl moiety, under those conditions wherein the hydroxymethyl-substituted compound is prepared, the formyl moiety undergoes hydrogenation to prepare a second hydroxymethyl moiety.

In the embodiment where an α-unsaturated acetal is the olefin, the products are generally formyl-substituted acetals, hydroxymethyl-substituted acetals or mixtures thereof. The formyl-substituted acetals generally correspond to the formulas

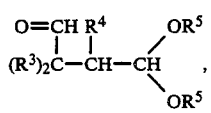

or

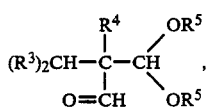

and the hydroxymethyl-substituted acetal corresponds to the formula

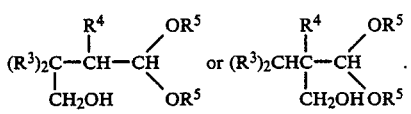

wherein R³, R⁴ and R⁵ are as defined hereinbefore.

Examples of such products include 4,4-dimethoxybutanal, 4,4-diethoxybutanal, 4,4-dimethoxybutanol and 4,4-diethoxybutanol. In the embodiment wherein R³ is hydrogen, the substitution on the α-unsaturated acetal occurs primarily on the β carbon atom. The hydroxymethyl acetal is the preferred product of this process.

Formyl refers herein to a carboxaldehyde moiety which corresponds to the formula

Hydrocarbyl means herein an organic radical containing carbon and hydrogen atoms. The term hydrocarbyl includes the following organic radicals: alkyl, alkenyl, alkynyl, cycloalkyl, cycloalkenyl, aryl, aliphatic and cycloaliphatic aralkyl and alkaryl. Aliphatic refers herein to straight- and branched-, and saturated and unsaturated, hydrocarbon chains, that is, alkyl, alkenyl or alkynyl. Cycloaliphatic refers herein to saturated and unsaturated cyclic hydrocarbons, that is, cycloalkenyl and cycloalkyl. The term aryl refers herein to biaryl, biphenylyl, phenyl, naphthyl, phenanthranyl, anthranyl and two aryl groups bridged by an alkylene group. Alkaryl refers herein to an alkyl-, alkenyl- or alkynyl-substituted aryl substituent wherein aryl is as defined hereinbefore. Aralkyl means herein an alkyl, alkenyl or alkynyl group substituted with an aryl group, wherein aryl is as defined hereinbefore. $C_{1-20}$ alkyl includes straight- and branched-chain methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl and eicosyl groups. $C_{1-5}$ alkyl includes methyl, ethyl, propyl, butyl and pentyl.

Cycloalkyl refers to alkyl groups containing one, two, three or more cyclic rings. Cycloalkenyl refers to mono-, di- and polycyclic groups containing one or more double bonds. Cycloalkenyl also refers to cycloalkenyl groups wherein two or more double bonds are present.

The novel catalyst of this invention comprises a mixture of (a) an alkali metal iron carbonyl or an alkaline earth metal iron carbonyl compound which corresponds to the formula $M_a[Fe_x(CO)_y]$, and (b) an iron pentacarbonyl wherein M is an alkali metal or alkaline earth metal; a is 1 or 2; x is 2, 3 or 4; and y is 8, 11 or 13. Preferred alkali metal iron carbonyl or alkaline earth metal iron carbonyl compounds include $M_2Fe_2(CO)_8$, $M_2Fe_3(CO)_{11}$ and $M_2Fe_4(CO)_{13}$. Preferably, x is 2 and y is 8. Wherein M is an alkali metal cation, a is 2, and wherein M is an alkaline earth metal, a is 1. Alkali metal refers herein to lithium, sodium, potassium, rubidium and cesium. Alkaline earth metal refers herein to beryllium, magnesium, calcium, strontium or barium. M is preferably an alkali metal, more preferably potassium, sodium or lithium, and most preferably potassium.

The relative ratio of the catalyst components can be any ratio which provides a catalyst which effectively catalyzes the reaction. Preferably, the molar ratio of the iron pentacarbonyl to the alkali metal or alkaline earth metal iron carbonyl compound is between about 0.01:1.0 to 10:1 and more preferably between 1.0:1.0 and 10.0:1.0.

The catalyst is prepared by dissolving an iron nonacarbonyl compound which corresponds to the formula $Fe_x(CO)_z$ in a suitable solvent which contains at least an equivalent amount of an alkali metal base or alkaline earth metal base (hydroxide and the like) to prepare the alkali metal iron carbonyl or alkaline earth metal iron carbonyl compound. To this solution is added iron pentacarbonyl.

A catalytic amount of the catalyst composition is that amount which catalyzes the reaction. Preferably, a catalytic amount of the catalyst is between about 0.1 and 30 mole percent based upon the olefin and more preferably between about 1 and 10 mole percent.

The hereinbefore olefins are reacted with carbon monoxide and water under conditions such that a formyl or hydroxymethyl group is inserted at the point of unsaturation. In general, to get complete conversions, at least a stoichiometric amount of carbon monoxide and water is required. It is advantageous to use an excess of carbon monoxide and in some embodiments the reactor is pressurized with excess carbon monoxide. If too much water is used, unwanted by-products are formed. The amount of water used is that amount which is sufficient to provide the desired conversion and which does not result in the formation of unwanted by-products. Preferably, between about 1 and 5 moles of water per mole of olefin is used, most preferably between about 1 and 3.

It is believed that this reaction proceeds by a two-step sequence. In the first step a formyl group is inserted on the double bond. In the second step, the formyl group is hydrogenated to a hydroxymethyl group. By controlling the reaction conditions, the relative amounts of formyl- and hydroxymethyl-substituted products can be controlled.

In general, the olefin is dissolved in a polar organic solvent, contacted with the catalyst and exposed to reaction conditions. The catalyst can be added to the solvent after addition of the olefin or the catalyst may be present in the solvent when the olefin is added.

The temperatures suitable for this reaction are those at which the reaction proceeds. Preferable temperatures are between 80° C. and 140° C. At temperatures below 80° C., the reaction rate is slow. At temperatures above 140° C., the formation of undesirable by-products takes place. At temperatures below 120° C., hydrogenation is very slow, whereas above 120° C., the formyl group undergoes hydrogenation to the hydroxymethyl group. As the temperature is increased, the overall conversion increases.

The reaction is pH sensitive. It is preferable to run the reaction at a pH of greater than 6, more preferable at a pH of 6 to 9, with a pH of 6 to 8 being most preferable. A neutral pH gives the optimum results. Below a pH of 6, the reaction does not proceed.

The process may be run at any pressure wherein the reaction proceeds. Preferable pressures are between about 14.7 and 5000 psi, more preferably between about 50 and 1000 psi, most preferably between about 100 and 300 psi.

Suitable reaction times are those which give the desired product yield. Preferable reaction times are between 30 and 300 minutes. Generally under suitable conditions, longer reaction times result in a greater conversion of olefin to the hydroxymethyl-substituted product over the formyl-substituted product.

Suitable solvents for this process are polar organic solvents. Examples of such solvents are alkanols, ethers, amides and glycol ethers. Preferred solvents are alkanols such as methanol, ethanol, propanol, butanol and the like, with ethanol being most preferred.

A by-product of this process is carbon dioxide, which can temporarily deactivate the catalyst. It is desirable to purge the reactor with carbon monoxide or an inert gas to remove the carbon dioxide from the reactor. It is advantageous to run this process in the absence of oxygen-containing gases. This is done by running the reaction in a carbon monoxide, inert gas, or a mixed carbon monoxide and hydrogen atmosphere.

SPECIFIC EMBODIMENTS

The following examples are included for illustrative purposes only and do not limit the scope of the claims or invention. Unless otherwise stated, all parts and percentages are by weight.

EXAMPLES 1-6

Procedure of Examples 1 to 6:

The reactor used for these examples is a 180 cc Aminco rocking autoclave with a removable glass linear. In all examples, the reactor is sealed after pressurization with carbon monoxide and the pressure is allowed to fluctuate according to temperature changes and gas consumption. A catalyst solution is prepared by dissolving 0.19 g (0.52 mmole) of $Fe_2(CO)_9$ in 1.9 ml of an ethanolic potassium hydroxide (KOH) solution (0.55 molar). A 0.50-ml portion of the resulting dark reddish-brown solution is added to 0.15 ml of $Fe(CO)_5$ and 2.50 ml of ethanol in a glass liner. Then, 1.30 g (10 mmoles) of 3,3-diethoxypropene-1 and 0.50 ml (28 mmoles) of $H_2O$ are added to the liner. All of the above operations are carried out under an atmosphere of $N_2$. The glass liner is sealed in a 180 cc rocking autoclave which is subsequently flushed with carbon monoxide then pressurized with 210 psig of carbon monoxide. The reaction mixture is agitated by rocking while the autoclave is heated to different reaction temperatures and maintained at that temperature for one hour. After the reactor cools, the solution inside the liner is analyzed by gas chromatography.

Table I describes the specific runs and the results.

TABLE I

| | | Product Solution Composition Weight[1] Percent | | | | | | | |
|---|---|---|---|---|---|---|---|---|---|
| Example | Temp (°C.) | 3,3-di-ethoxy propene-1 | 3,3-di-ethoxy propane | 4,4-di-ethoxy butanal | 4,4-di-ethoxy butanol | 3,3-di-ethoxy 1-methyl propanal | Con-version[2] | Selec-tivity[3] | Ratio of Linear to Branched Products |
| 1 | 90 | 96.0 | — | 2.8 | — | 0.3 | 4.0 | 78.0 | 10/1 |
| 2 | 100 | 70.6 | — | 19.8 | — | 1.1 | 29.4 | 71.1 | 18/1 |
| 3 | 110 | 40.1 | 8.8 | 25.0 | — | 1.0 | 59.9 | 43.3 | 25/1 |
| 4 | 120 | 30.7 | 11.7 | 35.2 | — | 1.1 | 69.1 | 52.5 | 32/1 |
| 5 | 130 | 11.6 | 17.1 | 39.0 | 5.6 | 1.0 | 88.4 | 51.6 | 37/1 |
| 6 | 140 | 5.0 | 18.7 | 31.6 | 11.6 | — | 95.0 | 45.1 | |

[1]Percentages are computed excluding the solvent.
[2]Conversion is the mole percentage of the 3,3-diethoxypropene-1 consumed to product.
[3]Selectivity refers to the mole percentage of 4,4-diethoxybutanal and 4,4-diethoxybutanol in the converted product.

EXAMPLES 7-10

A series of examples are run in the manner described in Examples 1-6 except that 3.5 ml of ethanol is used as the solvent. The examples are carried out at 110° C., and with varied initial pressures. The results of these examples are described in Table II.

TABLE II

| | | | Selectivity | | | |
|---|---|---|---|---|---|---|
| Example | Initial Pressure (psig) | Conversion (weight %) | 4,4-diethoxy-butanal (weight %) | 3,3-diethoxy-1-methyl propanal (weight %) | 3,3-diethoxy-propane (weight %) | ethyl-propanoate (weight %) |
| 7 | 50 | 91.2 | 25.5 | 0.8 | 15.9 | 52.6 |
| 8 | 100 | 70.5 | 47.8 | 4.7 | 20.1 | 22.3 |
| 9 | 200 | 54.9 | 51.4 | 1.0 | 18.0 | 13.1 |
| 10 | 400 | 10.8 | 73.1 | 3.1 | — | 8.3 |

EXAMPLE 11

A catalyst solution is prepared by dissolving 0.15 g (0.41 mmole) of $Fe_2(CO)_9$ in 1.5 ml of a methanolic KOH solution (0.55 molar). A 0.50-ml portion of the resulting dark reddish-brown solution is added to 0.50 ml of $Fe(CO)_5$ and 2.5 ml of $CH_3OH$ in a glass liner. Then, 1.2 g (10 mmoles) of norbornene carboxaldehyde and 0.50 ml (28 mmoles) of $H_2O$ are added to the liner. All of the above operations are carried out under an atmosphere of $N_2$. The glass liner is sealed in a 180 cc rocking autoclave which is subsequently flushed with carbon monoxide, then pressurized with 200 psig of carbon monoxide. The reaction mixture is agitated by rocking while the autoclave temperature is raised to 110° C., and maintained at that temperature for 50 minutes then allowed to cool. After gas chromatographic analysis, another 0.50 ml of $H_2O$ is added to the liner and the liner is returned to the reactor which is sealed and pressurized to 204 psig with carbon monoxide. The reactor temperature is raised to 110° C. for 45 minutes, with agitation, then allowed to cool. After gas chromatographic analysis, the liner is again returned to the reactor, pressurized to 200 psig with carbon monoxide and heated to 110° C., with agitation, for 45 minutes. The results of these reactions are shown in Table III.

TABLE III

| | Product Solution Composition (weight %)* | | | | |
|---|---|---|---|---|---|
| Reaction Time (min.) | Norbornene carboxaldehyde | Norbornene hydroxymethyl | Norbornene dicarboxaldehyde | Hydroxymethyl Norbornene carboxaldehyde | Norbornene dimethanol |
| 50 | 62.0 | 4.5 | 21.2 | 3.0 | 2.9 |
| 95 | 44.0 | 6.2 | 28.7 | 8.1 | 5.8 |
| 140 | 33.8 | 6.1 | 30.7 | 12.7 | 7.3 |

*Excluding solvent.

What is claimed is:

1. A process for the hydroformylation of $C_{2-4}$ alkenes, formyl-substituted $C_{2-4}$ alkenes, aryl-substituted alkenes, unsaturated norbornane ring-containing compounds, and α-unsaturated acetals which comprises contacting a $C_{2-4}$ alkene, a formyl-substituted $C_{2-4}$ alkene, aryl-substituted alkene, an unsaturated norbornane ring-containing compound or an α-unsaturated acetal in a polar organic solvent with water and carbon monoxide in the presence of a catalytic amount of a catalyst which comprises a mixture of (a) an alkali metal iron carbonyl or alkaline earth metal iron carbonyl or a mixture thereof which corresponds to the formula $M_a$-$Fe_x(CO)_y$ and (b) iron pentacarbonyl under conditions such that an alcohol or aldehyde derivative of a $C_{2-4}$ alkene, a formyl-substituted $C_{2-4}$ alkene, an aryl-substituted alkene, unsaturated norbornane ring-containing compound or an α-unsaturated acetal, is prepared wherein M is an alkali metal or alkaline earth metal; a is 1 or 2; x is an integer of 2 to 4, inclusive; and y is 8, 11 or 13.

2. The process of claim 1 wherein the catalyst comprises a molar ratio of (a) an alkali metal iron carbonyl or alkaline earth metal iron carbonyl or a mixture thereof to (b) iron pentacarbonyl of between about 1:0.1 and 1:10.

3. The process of claim 2 wherein x is 2 and y is 8.

4. The process of claim 3 wherein the alkali metal iron carbonyl is sodium iron octacarbonyl, lithium iron octacarbonyl or potassium iron octacarbonyl.

5. The process of claim 4 wherein the alkali metal iron carbonyl is potassium iron octacarbonyl.

6. The process of claim 4 wherein a catalytic amount of the catalyst is between about 0.1 and 30 mole percent.

7. The process of claim 6 wherein a catalytic amount of the catalyst is between about 1 and 10 mole percent.

8. The process of claim 7 wherein the temperature is between about 90° C. and 140° C.

9. The process of claim 8 wherein the pressure is between about 14.7 and 5000 psi.

10. The process of claim 9 wherein the polar organic solvent is a glycol ether, alkanol, cyclic ether or aliphatic ether.

11. The process of claim 10 wherein the polar organic solvent is an alkanol.

12. The process of claim 1 wherein a $C_{2-4}$ alkene, a $C_{2-4}$ formyl-substituted alkene, or an aryl-substituted alkene is hydroformylated under conditions such that an alcohol or aldehyde derivative or mixture thereof of the alkenes is prepared.

13. The process of claim 12 wherein the alkene corresponds to the formula

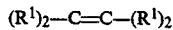

the alcohol derivative of the alkene corresponds to the formula

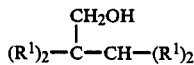

and the aldehyde derivative corresponds to the formula

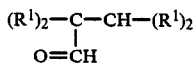

wherein $R^1$ is separately in each occurrence hydrogen, methyl, ethyl, a formyl moiety, a phenyl group or a phenyl group substituted with an alkyl, aryl, halo, nitro, cyano, formyl, alkoxy or aryloxy group.

14. The process of claim 12 wherein the product is an alcohol derivative of the alkene.

15. The process of claim 1 wherein an unsaturated norbornane ring-containing compound is hydroformylated under conditions such that a formyl-substituted norbornane ring-containing compound, a hydroxymethyl-substituted norbornane ring-containing compound or a mixture thereof is prepared.

16. The process of claim 15 wherein the unsaturated norbornane ring-containing compound corresponds to one of the formulas,

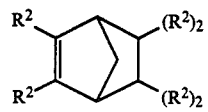

or

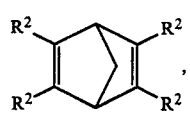

the formyl-substituted norbornane ring-containing compound corresponds to one of the formulas

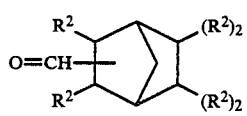

or

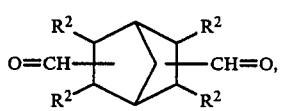

and the hydroxymethyl-substituted norbornane ring-containing compound corresponds to one of the formulas

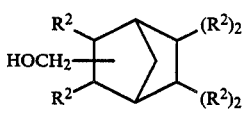

or

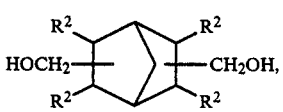

wherein $R^2$ is separately in each occurrence hydrogen, a formyl group, a hydroxymethyl or a $C_{1-20}$ hydrocarbyl group, and wherein two $R^2$'s together on adjacent carbon atoms may form a ring structure.

17. The process of claim 16 wherein the unsaturated norbornane ring-containing compound is hydroformylated under conditions such that a hydroxymethyl-substituted norbornane ring-containing compound is prepared.

18. The process of claim 17 wherein an unsaturated norbornane ring-containing compound with one $R^2$ which a formyl substituent and the remaining $R^2$'s are hydrogen, is hydroformylated under conditions such that a dihydroxymethyl norbornane ring-containing compound is prepared.

19. The process of claim 1 wherein an α-unsaturated acetal is hydroformylated under conditions such that a formyl-substituted acetal, hydroxymethyl-substituted acetal or a mixture thereof is prepared.

20. The process of claim 19 wherein the α-unsaturated acetal corresponds to the formula

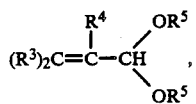

the formyl-substituted acetal corresponds to the formula

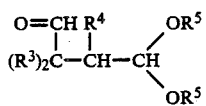

or

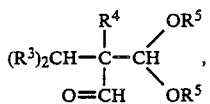

and the hydroxymethyl-substituted acetal corresponds to the formula

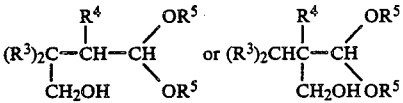

wherein $R^3$ is hydrogen or $C_{1-20}$ alkyl; $R^4$ is hydrogen or methyl; and $R^5$ is $C_{1-20}$ hydrocarbyl; or both $R^5$'s may combine to form a cyclic acetal ring.

21. The process of claim 20 wherein the α-unsaturated acetal is hydroformylated under conditions such that a hydroxymethyl-substituted acetal is prepared.

* * * * *